United States Patent
Ohsaki et al.

(10) Patent No.: US 6,605,045 B2
(45) Date of Patent: Aug. 12, 2003

(54) WRISTWATCH-TYPE HUMAN PULSE WAVE SENSOR ATTACHED ON BACK SIDE OF USER'S WRIST

(75) Inventors: Rie Ohsaki, Anjo (JP); Teiyuu Kimura, Nagoya (JP); Naoki Fukaya, Obu (JP)

(73) Assignee: Denso Corporation, Kariya (JP)

( * ) Notice: Subject to any disclaimer, the term of this patent is extended or adjusted under 35 U.S.C. 154(b) by 169 days.

(21) Appl. No.: 09/852,698

(22) Filed: May 11, 2001

(65) Prior Publication Data

US 2001/0056243 A1 Dec. 27, 2001

(30) Foreign Application Priority Data

Jun. 14, 2000 (JP) ........................................ 2000-177999

(51) Int. Cl.[7] ............................................. A61B 5/0245
(52) U.S. Cl. ..................................................... 600/503
(58) Field of Search ................................. 600/503, 500, 600/344

(56) References Cited

U.S. PATENT DOCUMENTS 4,901,733 A * 2/1990 Kaida et al. ................. 128/687

2002/0151775 A1 * 10/2002 Kondo ........................ 600/344

FOREIGN PATENT DOCUMENTS

| DE | 2824899 | * 12/1979 |
| JP | 2-213325 | * 8/1990 |
| JP | 11-70087 | 3/1999 |
| JP | 11-235320 | * 8/1999 |
| JP | 2001-276000 | * 10/2001 |

* cited by examiner

*Primary Examiner*—John A. Jeffery
(74) *Attorney, Agent, or Firm*—Posz & Bethards, PLC

(57) ABSTRACT

A pulse wave sensor includes a detecting element and a sensor body. The pulse wave sensor is worn on the back side of a user's wrist corresponding to the back of the user's hand. The detecting element includes a translucent member on its top, and the translucent member has a convex surface. The detecting element is attached on the back side of the user's wrist by a dedicated belt so that the convex surface of the translucent member is in intimate contact with the surface of the user's skin. The sensor body is attached on the back side of the user's wrist by another dedicated belt so that it is arranged on the detecting element. A cushion is arranged between the sensor body and the detecting element. The pulse wave sensor can stably detect the pulse wave without being affected by the movement of the user's wrist.

6 Claims, 2 Drawing Sheets

WRISTWATCH-TYPE HUMAN PULSE WAVE SENSOR ATTACHED ON BACK SIDE OF USER'S WRIST

CROSS REFERENCE TO RELATED APPLICATION

This application is based on and incorporates herein by reference Japanese Patent Application No.2000-177999 filed on Jun. 14, 2000.

BACKGROUND OF THE INVENTION

1. Field of the Invention

The present invention relates to an optical sensor for detecting the pulse wave of a human body.

2. Related Art

JP-A-11-70087 proposes a wristwatch-type device for detecting the pulse wave of a human body. This detecting device is worn on the user's wrist. The device includes a detecting element for detecting a pulse wave and a sensor body including a display. The detecting element is fixed on the front side of the user's wrist corresponding to the palm of the user's hand by a band attached to the sensor body. The information of pulse wave detected by the detecting element is displayed on the display of the sensor body fixed on the back side of the user's wrist.

The two bones (the radius and the ulna) pass through the front side of the user's wrist. Therefore the detecting element has a tendency to slip off the detection position of the user's wrist, since the skin surface of the front side of the user's wrist greatly moves as the user's wrist moves. Furthermore, the user feels uncomfortable since the radius and the ulna are pressed. As a result, the user further moves his/her wrist unconsciously and it becomes further difficult to detect the pulse wave stably.

SUMMARY OF THE INVENTION

The present invention overcomes the above drawbacks, and has an object to provide a human pulse wave sensor which is capable of detecting the pulse wave of a human body stably and has high detection probability.

The pulse wave sensor according to the present invention includes a detecting element and a sensor body. The pulse wave sensor is worn on the back side of the user's wrist corresponding to the back of the user's hand for detecting the pulse wave of the user. The detecting element includes a light emitting element and a light receiving element. The sensor body is connected to the detecting element by a signal line.

Preferably, a translucent member is arranged on the light emitting element and the light receiving element. The translucent member has a convex surface. The detecting element is attached on the back side of the user's wrist by a dedicated belt so that the convex surface of the translucent member is in intimate contact with the surface of the user's skin. The light emitting element and the light receiving element are arranged in the longitudinal direction of the user's arm. The sensor body is attached on the back side of the user's wrist by a dedicated belt other than the belt of the detecting element so that it is arranged on the detecting element. A cushion is arranged between the sensor body and the detecting element.

According to this construction, the user does not feel uncomfortable when the pulse wave sensor is worn on the user's wrist. Furthermore the detecting element is fixed on the user's wrist without slipping off the detection position of the user's wrist, even if the user is in motion. Accordingly the pulse wave sensor can stably detect the pulse wave of the user.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENT

Figure 1:
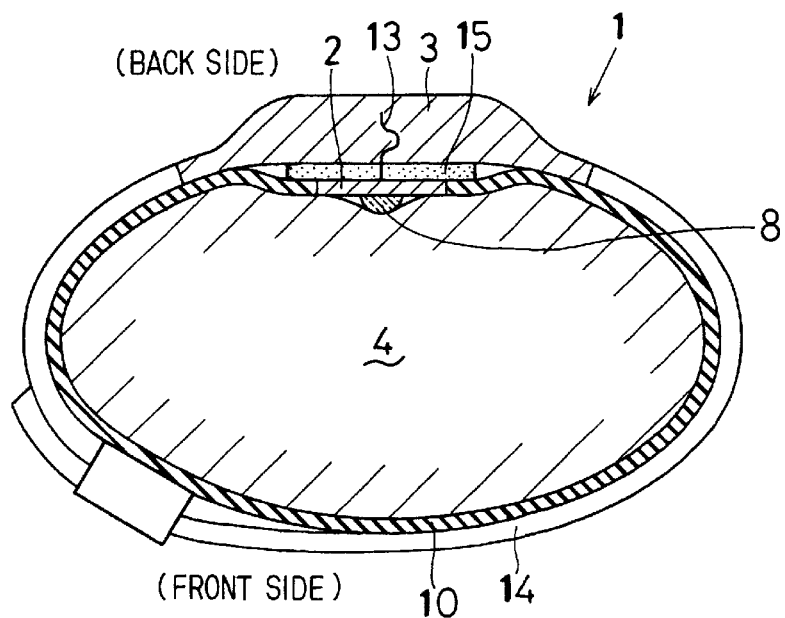
FIG. 1 is a cross-sectional view of a pulse wave sensor attached on the user's wrist.

Referring to FIG. 1, a pulse wave sensor 1 includes a detecting element 2 and a sensor body 3. The pulse wave sensor 1 is worn on the back side of the user's wrist 4 corresponding to the back of the user's hand in the similar manner as a wristwatch is normally worn. This sensor 1 is used for detecting the pulse wave of the user's body for a medical diagnosis, a physical check up, and the like.

Figure 2:
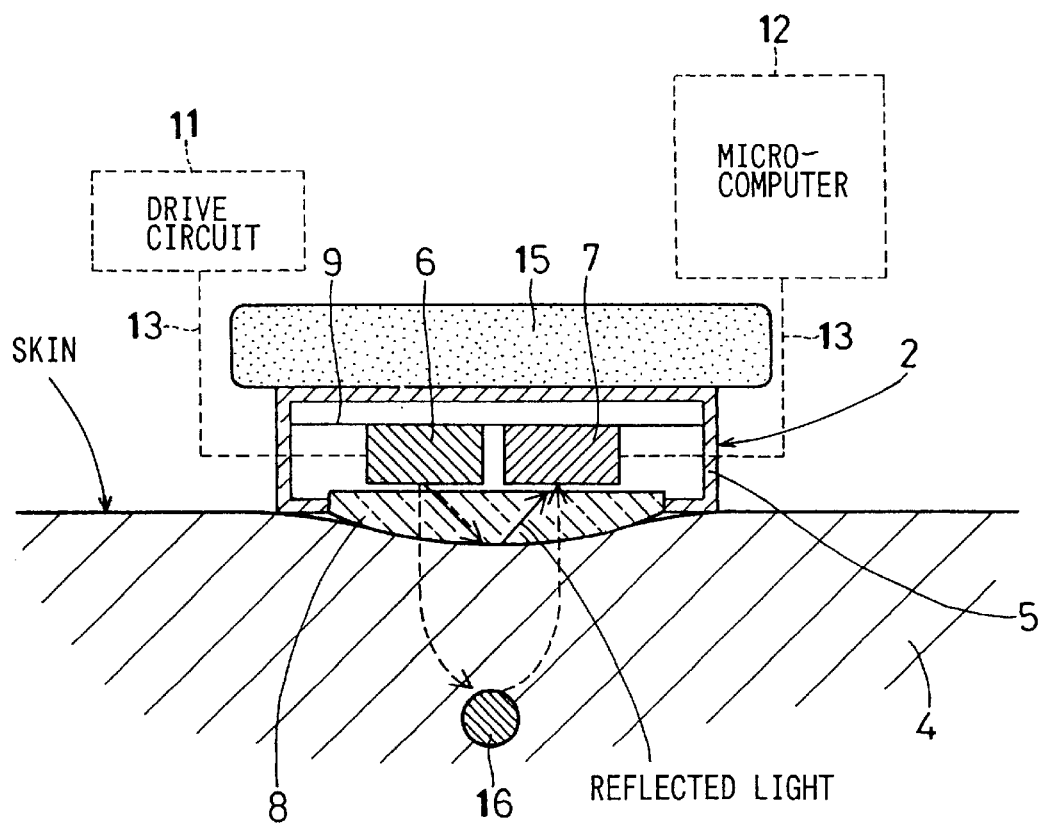
FIG. 2 is a schematic diagram of a mechanism for detecting a pulse wave.

Referring to FIG. 2, the detecting element 2 comprises a package 5, a light emitting element 6 (e.g., LED), a light receiving element 7 (e.g., PD), and a translucent board 8. The package 5 has an opening and includes a circuit board 9 therein. The light emitting element 6 and light receiving element 7 are included in the package 5 and arranged on the circuit board 9. The translucent board 8 is a glass board which is transparent to light, and attached to the opening of the package 5. A convex surface is formed on the top of the translucent board 8 as shown in FIG. 2.

The detecting element 2 is fixed on the user's wrist 4 by a dedicated belt 10 attached to the detecting element 2 as shown in FIG. 1. The belt 10 may be made from elastic material so that regular pressure is applied to the user's wrist 4. In this case, light reflected by the surface of the skin or disturbance light from the outside is prevented from penetrating the translucent board 8, since the surface of the translucent board 8 is in intimate contact with the surface of the user's skin. However the user feels uncomfortable if the pressure applied to the user's wrist 4 is too high. Therefore it is desirable that the pressure applied to the user's wrist 4 is limited to 5–15 mmHg.

The light emitting element 6 and the light receiving element 7 are arranged side by side as shown in FIG. 2. Accordingly the length of the detecting element 2 from the right side to the left side in FIG. 2 is longer than the length from the upper side to the lower side. If the detecting element 2 is arranged so that its longitudinal direction (from the right side to the left side in FIG. 2) agrees with the circumferential direction of the user's wrist 4, it has a tendency to slip off. Therefore it is desirable that the detecting element 2 is arranged so that its longitudinal direction agrees with the longitudinal direction of the user's arm. The dedicated belt 10 is attached to the detecting element 2 so that it can fix the detecting element 2 on the user's wrist 4 in this way.

The sensor body 3 is connected to the detecting element 2 by a signal line 13, and includes, as shown in FIG. 2, a drive circuit 11, a microcomputer 12, and a monitor display (not shown). The drive circuit 11 drives the light emitting element 6 to emit light toward the wrist 4. The microcomputer 12 calculates the pulse rate from the reflected light received by the detecting element 2. This reflected light varies with the user's pulsation. The monitor display shows the calculated pulse rate and the like.

The sensor body 3 is arranged on the top of the detecting element 2, and fixed on the user's wrist 4 by a dedicated belt 14 attached to the sensor body 3. A cushion 15 such as a sponge or a gel is inserted between the detecting element 2 and the sensor body 3 so that the detecting element 2 does not directly contact the sensor body 3.

The pulse wave sensor 1 detects the pulse wave of the user's body as follows. The light emitting element 6 emits light toward the user's wrist 4, a portion of the emitted light penetrates the capillary arteriole 16 in the inside of the user's wrist 4 and is absorbed by the haemoglobin in the blood. The rest of the emitted light is reflected and scattered by the capillary arteriole 16, and partly reaches the light emitting element 7. As the amount of the haemoglobin in the blood varies in waves due to the pulsation of the user's blood, the amount of the light absorbed by the haemoglobin also varies in waves. As a result, the amount of the light which is reflected by the capillary arteriole 16 and reaches the light receiving element 7 varies in waves. This variation in the amount of the light received by the light receiving element 7 is detected as the pulse wave information.

Figure 3A:
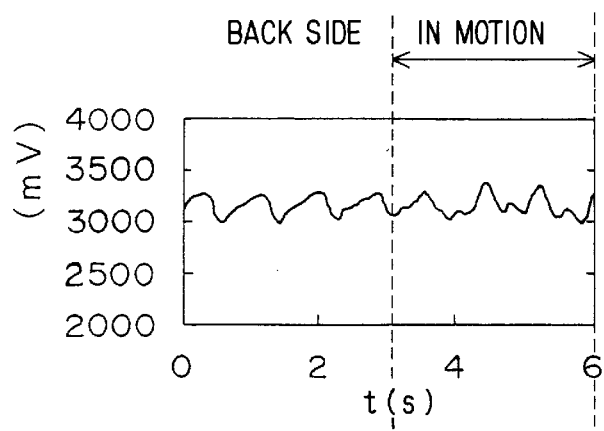
FIGS. 3A and 3B are graphs of the pulse wave detected by a pulse wave sensor attached on the back side of the user's wrist and the pulse wave detected by a pulse wave sensor attached on the front side of the user's wrist, respectively.
Figure 3B:
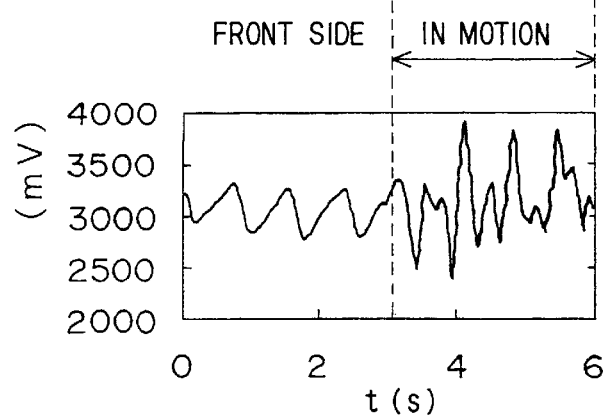

If the detecting element 2 is arranged on the front side of the user's wrist 4, the amount of the light received by the light receiving element 7 is increased. That is, the intensity of the signal received by the light receiving element 7 is increased. However, the detecting his/her wrist, and therefore the intensity of the light received by the light receiving element 7 largely varies depending on the shift amount of the detecting element 2. As shown in FIG. 3B, in the case that the detecting element 2 is arranged on the front side of the user's wrist 4, the pulse wave can be detected well if the user is at rest. However, when the user is in motion, the detected pulse wave is adversely affected by the movement of the user's wrist 4.

In contrast to this, if the detecting element 2 is arranged on the back side of the user's wrist 4, the user will not move his/her wrist unconsciously since the radius and the ulna inside the user's wrist 4 are not pressed and consequently the user does not feel so uncomfortable. Further, the detecting element 2 will not shift so widely even if the user's wrist moves. Therefore the detecting element 2 is stably fixed to the detecting position of the user's wrist 4. As a result, the pulse wave is detected stably without being affected by the movement of the user's wrist 4 as shown in FIG. 3A.

Figure 4A:
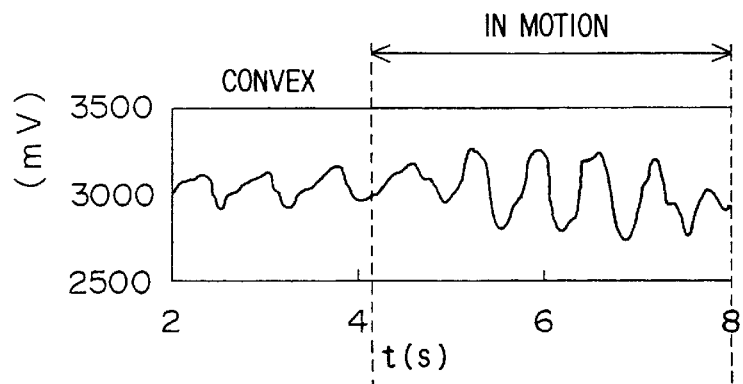
FIGS. 4A and 4B are graphs of the pulse wave detected by a pulse wave sensor including a convex detecting surface and the pulse wave detected by a pulse wave sensor including a flat detecting surface, respectively.
Figure 4B:
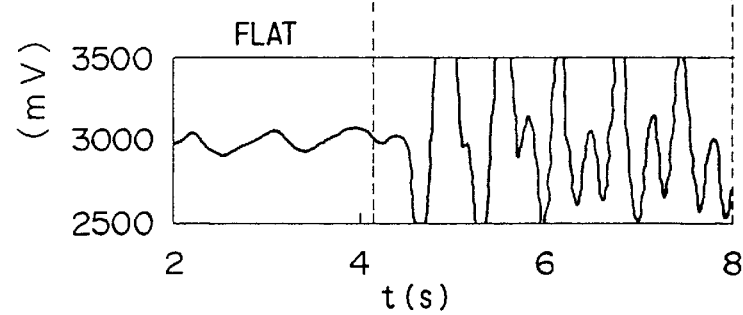

The detecting element 2 is arranged on the user's wrist 4 SO that the convex surface of the translucent board 8 is in intimate contact with the surface of the user's skin. Thereby it-is the detecting element 2 is preventing from slipping off the detecting position of the user's wrist 4. If the translucent board 8 has a flat surface, the detected pulse wave is adversely affected by the movement of the user's wrist 4 as shown in FIG. 4B. However, in the case that the translucent board 8 has a convex surface like the present embodiment, the variation of the amount of the reflected light which is emitted from the light emitting element 6 and reaches the light receiving element 7 by being reflected by the surface of the user's skin is suppressed. Noise such as disturbance light from the outside is prevented from penetrating the translucent board 8. Therefore the pulse wave can be detected without being affected by the movement of the user's wrist 4 as shown in FIG. 4A.

The detecting element 2 and the sensor body 3 is attached to theuser's wrist 4 by the dedicated belts 10 and 14, respectively. That is, the detecting element 2 and the sensor body 3 are allowed to move relatively. Further the cushion 15 is arranged between the detecting element 2 and the sensor body 3. Therefore, if force is applied to the sensor body 3 or the sensor body 3 moves, the force applied to the sensor body 3 or the movement of the sensor body 3 cannot be transmitted to the detecting element 2 easily.

Accordingly the detecting element 2 is stably fixed to the user's wrist 4. As a result, the pulse wave sensor can detect the pulse wave at a high S/N ratio, that is, it can provide high detection probability, not only when the user is at rest but also when the user is taking light exercise.

Modifications

In the above embodiment, the sensor body 3 need not include the microcomputer 12 if it includes a transmitter instead. In this case, the pulse wave information detected by the detecting element 2 is transmitted to a receiver by the transmitter. The sensor body 3 can be downsized and light in weight in this case and consequently the force applied to the sensor body 3 or the movement of the sensor body 3 cannot be transmitted to the detecting element 2 easily.

In the above embodiment, the detecting element 2 and the sensor body 3 may be worn on the back side of the user's forearm.

What is claimed is:

1. A pulse wave sensor for detecting a pulse wave of a human body comprising:

a detecting element including a light emitting element and a light receiving element, the detecting element being constructed to be worn on a back side of a user's wrist or a user's forearm, the detecting element including a translucent member which is transparent to light and arranged on the light emitting element and the light receiving element, the translucent member having a convex surface, and the translucent member is for being arranged on the back side of the user's wrist or the user's forearm so that the convex surface of the translucent member is in intimate contact with skin of the user; and a sensor body including a circuit connected to the detecting element via a signal line.

2. A pulse wave sensor for detecting a pulse wave of a human body comprising:

a detecting element including a light emitting element and a light receiving element; and a sensor body including a circuit connected to the detecting element via a signal line, wherein the detecting element is constructed to be worn on a user's wrist or a user's forearm, the pulse wave sensor further comprising:

a first belt for fixing the detecting element to the user's wrist or the user's forearm; and a second belt for fixing the sensor body to the user's wrist or the user's forearm.

3. A pulse wave sensor for detecting a pulse wave of a human body comprising:

a detecting element including a light emitting element and a light receiving element; and a sensor body including a circuit connected to the detecting element via a signal line, wherein the detecting element is constructed to be worn on a user's wrist or a user's forearm, wherein the sensor body is arranged on the detecting element, and wherein a cushion is arranged between the detecting element and the sensor body.

4. A pulse wave sensor for detecting a pulse wave of a human body comprising:

a detecting element being constructed to be worn on a user's wrist or a user's forearm and including a light emitting element and a light receiving element, the light emitting element and the light receiving element being arranged side by side in a longitudinal arm direction, the detecting element including a translucent member which is transparent to light and that is arranged on the light emitting element and the light receiving element, the translucent member having a convex surface and the translucent member for being arranged on the user's wrist or the user's forearm so that the convex surface of the translucent member is in intimate contact with skin of the user; and a sensor body including a circuit connected to the detecting element via a signal line.

5. A pulse wave sensor as set forth in claim 4 further comprising:

a first belt for fixing the detecting element to the user's wrist or the user's forearm; and a second belt for fixing the sensor body to the user's wrist or the user's forearm.

6. A pulse wave sensor as set forth in claim 5, wherein:

the sensor body is arranged on the detecting element; and a cushion is arranged between the detecting element and the sensor body.

\* \* \* \* \*